US00PP32348P3

(12) United States Plant Patent
Brazelton et al.

(10) Patent No.: US PP32,348 P3
(45) Date of Patent: Oct. 20, 2020

(54) BLUEBERRY PLANT NAMED 'ZF08-029'

(50) Latin Name: *Vaccinium corymbosum*
Varietal Denomination: ZF08-029

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Hilo, HI (US)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 68 days.

(21) Appl. No.: 16/501,035

(22) Filed: Feb. 12, 2019

(65) Prior Publication Data

US 2019/0254205 P1 Aug. 15, 2019

Related U.S. Application Data

(60) Provisional application No. 62/710,226, filed on Feb. 13, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
None
See application file for complete search history.

*Primary Examiner* — Susan McCormick Ewoldt

(57) ABSTRACT

The new blueberry plant variety 'ZF08-029' is provided. 'ZF08-029' is a commercial variety intended for the hand harvest fresh fruit market. The variety is produced from a cross of 'G-344' (female parent, not patented) and 'Draper' (male parent, U.S. Pat. No. 15,103), which can be distinguished by its outstanding features.

6 Drawing Sheets

Latin name of the genus and species: *Vaccinium corymbosum.*

Variety denomination: The new blueberry plant claimed is of the variety denominated 'ZF08-029'.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry (*Vaccinium corymbosum* L. hybrid) plant, referred to as 'ZF08-029', as herein described and illustrated. 'ZF08-029' is a commercial blueberry variety intended for both the fresh and processed fruit markets. The variety has high plant vigor, a semi-sprawling, rounded growth habit, ripens mid-season, and produces medium sized fruit with good firmness. 'ZF08-029' was selected for its above average fruit quality, specifically its highly aromatic, peach type flavor.

'ZF08-029' has a more rounded and vigorous growth habit, and more flavorful, though smaller, fruit than 'Draper' (U.S. Pat. No. 15,103), the male parent. Compared to the female parent 'G-344' (not patented), 'ZF08-029' appears to be more tolerant to cold temperatures.

Pedigree and History: The new blueberry plant originated from a cross of 'G-344' (female parent, not patented) and 'Draper' (male parent) made in Lowell, Oreg., USA in 2004 and was selected in the same location in 2008.

The new blueberry variety 'ZF08-029' was initially propagated by softwood cuttings in 2008 from the original seedling in Lowell, Oreg., USA and planted in a replicated plot of nine plants in fall 2009. The plants established in Oregon were successfully used to establish in vitro culture lines in 2012

'ZF08-029' was selected in 2008 because of its high-quality fruit—firm, crisp, peachy flavor, light blue color, and medium size. Beginning in 2011, 'ZF08-029' was evaluated for seven years in Lowell, Oreg. for plant performance, fruit quality, and yield in comparison to standard varieties like 'Legacy' (not patented) and 'Draper'. Beginning in 2012, additional plots of 'ZF08-029' were established in other areas of Oregon, Northwest Washington and Central California. After extensive evaluation in these growing regions, 'ZF08-029' was determined to be sufficiently cold hardy and adaptable to varying soil conditions and commercial management strategies, and has a competitive yield for the harvest season. Plants of 'ZF08-029' propagated from softwood cuttings or in vitro are phenotypically stable and exhibit the same characteristics as the original plant.

SUMMARY OF THE INVENTION

The new blueberry plant variety 'ZF08-029' has not been observed under all possible environmental conditions. The phenotype may vary somewhat with variations in environment and cultural practices such as temperature and light intensity without, however, any variance in genotype.

'ZF08-029' is distinguished by a rounded, semi-sprawling growth habit, high vigor, and complex fruit flavor. The following characteristics of the new cultivar have been repeatedly observed and are determined to be the unique characteristics of the new blueberry plant variety 'ZF08-029':

1) Mid-season ripening
2) Medium, uniform fruit size
3) Aromatic, flavorful fruit with a firm texture

BRIEF DESCRIPTION OF THE DRAWINGS

The accompanying photographic illustration shows typical specimens in full color of the foliage and fruit of the new variety 'ZF08-029'. The colors are as nearly true as is reasonably possible in a color representation of this type.

Figure 1:
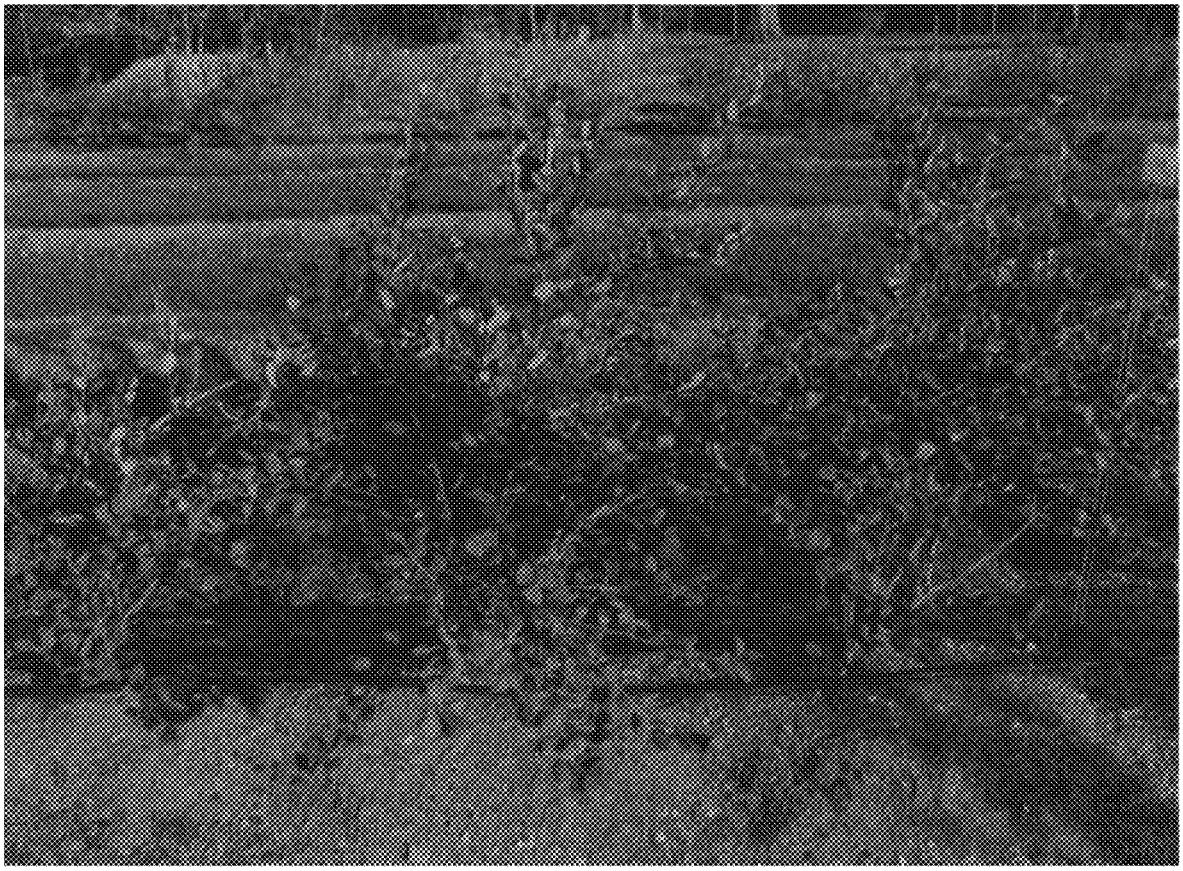
FIG. 1 is a photograph of the new variety 'ZF08-029', demonstrating the plant's leaves and growth habit in the fall. The plants were grown in Lowell, Oreg. and photographed on Nov. 18, 2014.
Figure 2:
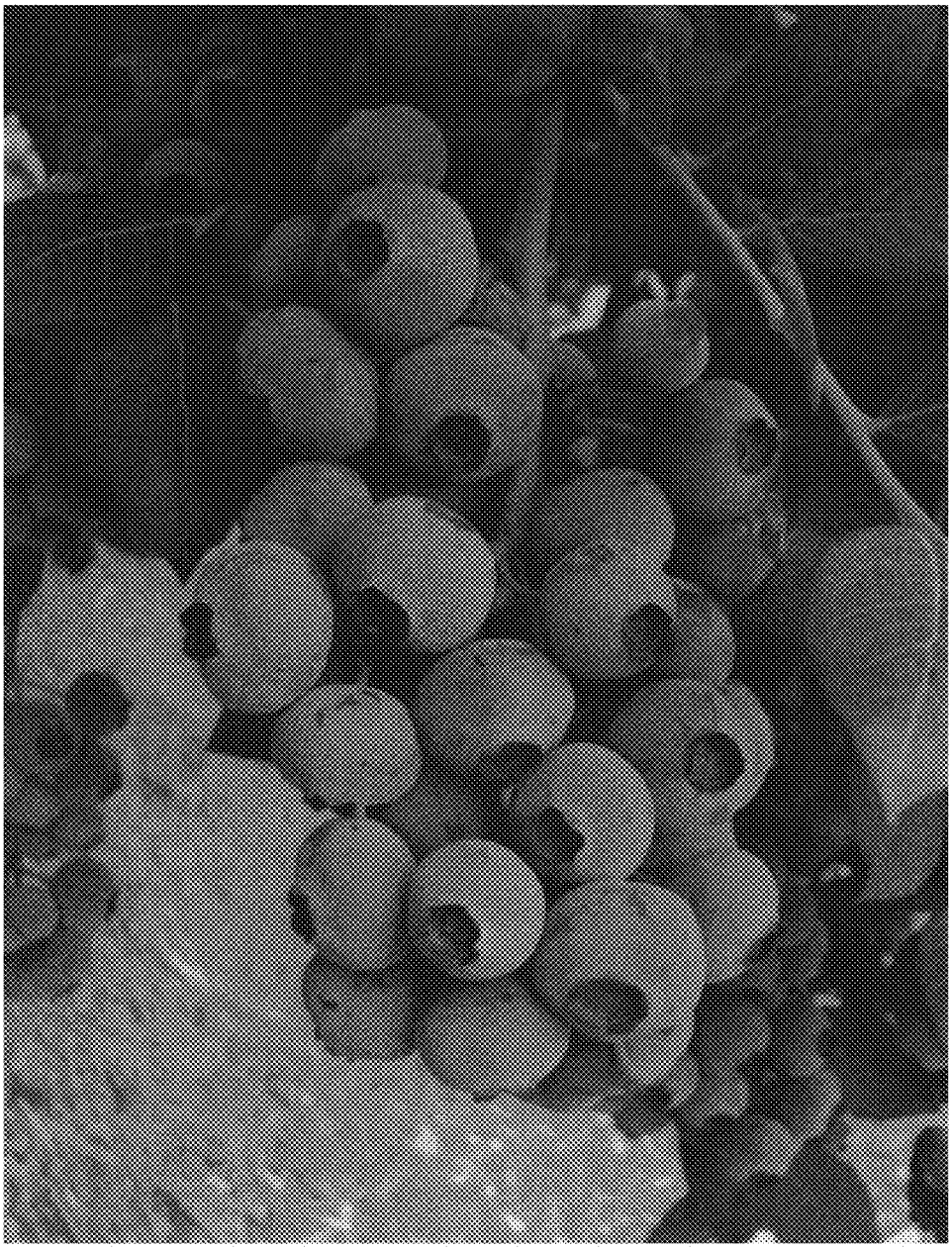
FIG. 2 is a photograph of the fruit cluster of the new variety 'ZF08-029' grown in Lowell, Oreg. and photographed on Jul. 3, 2014.
Figure 3:
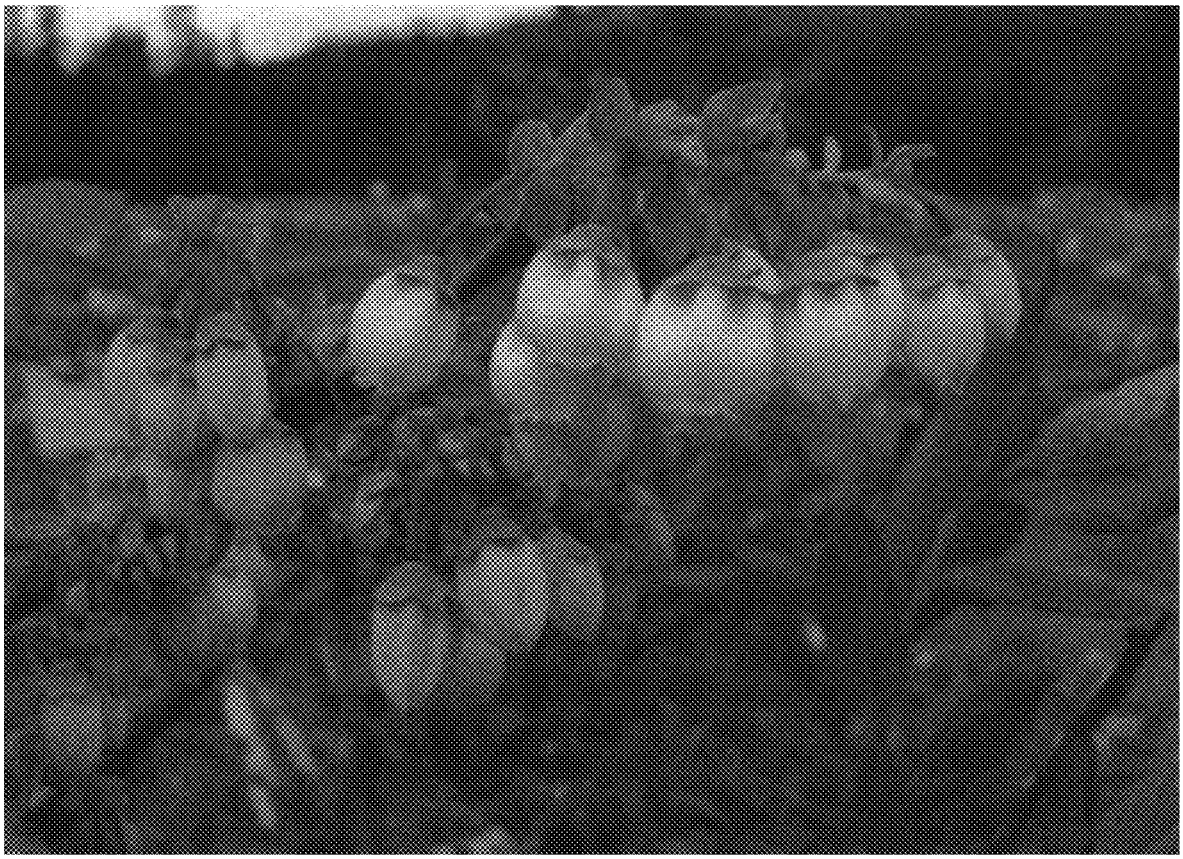
FIG. 3 is a photograph of the flowers of the new variety 'ZF08-029' grown in Lowell, Oreg. and photographed on Apr. 25, 2017.
Figure 4:
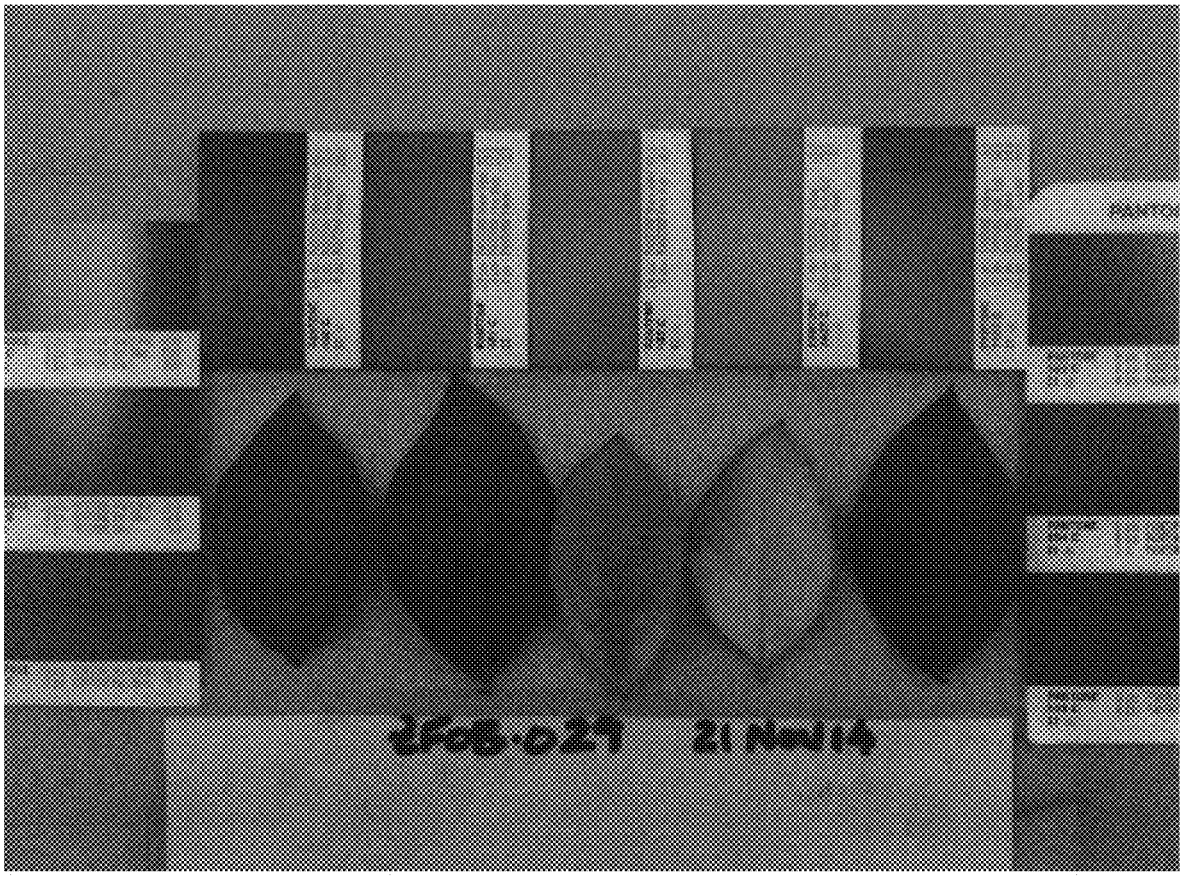
FIG. 4 is a photograph of the fall foliage of the new variety 'ZF08-029' grown in Lowell, Oreg. and photographed on Nov. 21, 2014.
Figure 5:
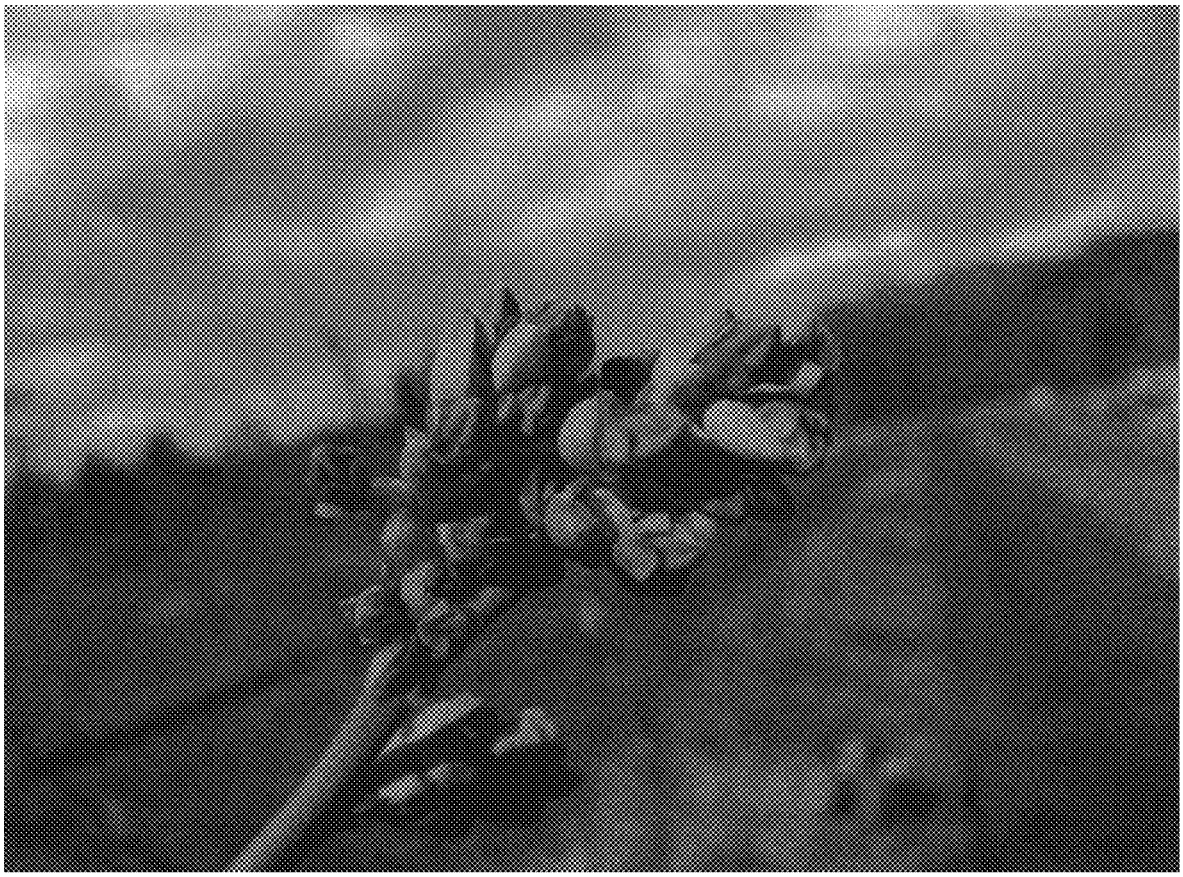
FIG. 5 is a photograph of early buds on the variety 'ZF08-029' grown in Lowell, Oreg. and photographed on Mar. 20, 2014.
Figure 6:
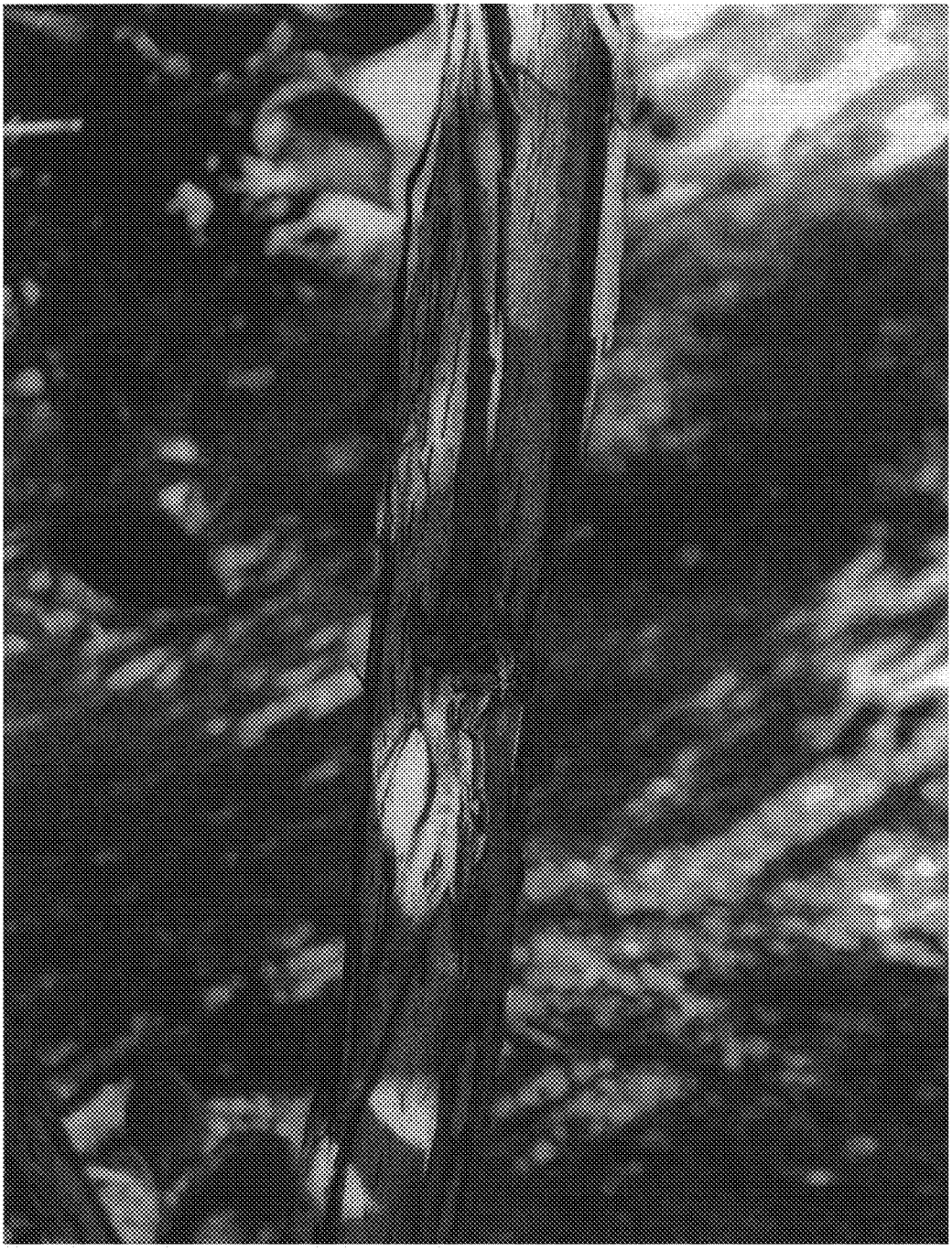
FIG. 6 is a photograph of the bark on the variety 'ZF08-029' grown in Lowell, Oreg. and photographed on Jul. 29, 2014.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'ZF08-029'. The data which define these characteristics were collected from asexual reproductions of the original selection. Dimensions, sizes, colors, and other characteristics are approximations and averages set forth as accurately as possible. The plant history was taken on plants approximately 5 years of age, unless otherwise noted, and the descriptions relate to plants grown in the field located at 39252 Jasper-Lowell Road, Lowell, Oreg., USA. Descriptions of fruit characteristics were made on fruit grown at the field described above. Color designations are from "The Pantone Book of Color" (by Leatrice Eiseman and Lawrence Herbery, Harry N. Abrams, Inc., Publishers, New York 1990). Where the Pantone color designations differ from the colors of the photographs, the Pantone colors are accurate.

Classification:

a. *Family*.—Ericaceae.
b. *Genus*.—*Vaccinium*.
c. *Species*.—*Corymbosum* hybrid.
d. *Common name*.—Northern Highbush Blueberry.

Parentage: Female Parent — 'G-344.' (not patented). Male Parent — 'Draper.' (U.S. Plant Pat. No. 15,103).

Market class: Fresh and process markets.

PLANT

General:

a. *Plant height*.—Average 1.33 m.
b. *Plant width*.—Average 1.52 m.
c. *Growth habit*.—Semi-sprawling.
d. *Growth*.—High vigor.
e. *Productivity*.—High. In Lowell, Oreg. on 3-year-old plants 6.13 lbs. per plant, compared to 'Legacy' (not patented) plants of the same age which produced an average of 8.40 lbs. per plant and 'Draper' plants which produced 4.54 lbs. per plant. On 4-year-old plants 'ZF08-029' produced 8.16 lbs. per plant, compared to 'Legacy' that produced an average of 9.92 lbs. per plant and 'Draper' that produced 4.71 lbs. per plant. On 5-year-old plants 'ZF08-029' produced 11.11 lbs. per plant while 'Legacy' produced 10.21 lbs. per plant and 'Draper' produced 6.62 lbs. per plant.
f. *Cold hardiness*.—Approximately USDA zones 6-8.
g. *Chilling requirement*.—Estimated minimum of 500-1000 hours below 45 degrees Fahrenheit.
h. *Leafing*.—Moderate.
i. *Twigginess*.—Low.
j. *Resistance/susceptibility to root rot* (*Phytopthora cinnamomii*).—Does not seem overly susceptible.
k. *Resistance/susceptibility to stem blight* (*botryosphaeria sp.*).—Does not seem overly susceptible.
l. *Resistance/susceptibility to Phomopsis twig blight* (*Phomopsis vaccinii*).—Does not seem overly susceptible.
m. *Resistance/susceptibility to Botrytis* (*Botrytis cinerea*).—Does not seem overly susceptible.
n. *Resistance/susceptibility to leaf spot* (*septoria spp.*).—Does not seem overly susceptible.
o. *Resistance/susceptibility to leaf rust* (*Naohidemyces vaccinii*).—Does not seem overly susceptible.
p. *Resistance/susceptibility to bud mites* (*Acalatus vaccinii*).—Undetermined.

STEM

General:

a. *Suckering tendency*.—Low.
b. *Mature cane color*.—Pantone colors Bark 16-1506, Ecur Drab 14-1212; Aztec 18-1130.
c. *Mature cane length*.—Average 0.45 m.
d. *Mature cane width*.—Average 1.82 cm.
e. *Bark texture*.—Rough.
f. *Fall color on new shoots*.—Pantone color Bitter Chocolate 19-1317.
g. *Surface texture of new wood*.—Smooth.
h. *Internode length on strong, new shoots*.—18.49 mm.
i. *Average number of buds per fruiting lateral*.—6.8.

FOLIAGE

General:

a. *Time of beginning of leaf bud burst*.—In Lowell, Oreg., mid-March.
b. *Leaf color* (*top side*).—Pantone color Burnt Olive 18-0521.
c. *Leaf color* (*under side*).—Pantone color Laden Green 18-0422.
d. *Leaf arrangement*.—Alternate.
e. *Leaf shape*.—Elliptic.
f. *Leaf margins*.—Entire.
g. *Undulation of margin*.—None.
h. *Leaf venation*.—Pinnate.
i. *Leaf apices*.—Acute.
j. *Leaf bases*.—Acute.

k. *Leaf length*.—Average 56.57 mm.
l. *Leaf width*.—Average 32.69 mm.
m. *Leaf length/width ratio*.—1.73 — medium.
n. *Leaf nectarines*.—Absent.
o. *Pubescence of upper side*.—None.
p. *Pubescence of lower side*.—None.
q. *Cross sectional profile*.—Flat.
r. *Longitudinal profile*.—Plane.
s. *Attitude*.—Spreading to ascending.
t. *Fall leaf color*.—Pantone color Bitter Chocolate 19-1317.

Petioles:
a. *Length*.—Average 2.83 mm.
b. *Width*.—Average 1.08 mm.
c. *Color*.—Pantone color Apple Green 15-0543.
d. *Petiole surface texture*.—Smooth.

FLOWERS

General:
a. *Time of beginning of flowering*.—Approximately early to mid-April in Lowell, Oreg.
b. *Time of* 50% *anthesis*.—Approximately late April to early May in Lowell, Oreg.
c. *Flower shape*.—Cylindrical to urceolate.
d. *Flower bud density*.—Medium.
e. *Flower fragrance*.—Sweet, faint.
f. *Immature flower color*.—Pantone colors Coral 17-1736 and Antique White 11-0105.

Corolla:
a. *Color*.—Pantone color Snow White 11-0602.
b. *Length*.—8.38 mm.
c. *Width*.—8.61 mm.
d. *Aperture width*.—4.64 mm.
e. *Anthocyanin coloration of corolla*.—Weak.
f. *Corolla ridges*.—Present.
g. *Protrusion of stigma*.—Even with lip of corolla to an average of 0.15 mm. above lip of corolla.

Inflorescence:
a. *Length*.—34.07 mm.
b. *Diameter*.—29.68 mm.
c. *Length of peduncle*.—19.46 mm.
d. *Surface texture of peduncle*.—Smooth.
e. *Color of peduncle*.—Pantone color Green Banana 14-0434.
f. *Length of pedicel*.—6.23 mm.
g. *Surface texture of pedicel*.—Smooth.
h. *Color of pedicel*.—Pantone colors Peridot 17-0336 and Green Oasis 15-0538.
i. *Number of flowers per cluster*.—9.
j. *Flower cluster density*.—Medium.

Calyx (with sepals):
a. *Diameter*.—6.03 mm.
b. *Color* (*sepals*).—Pantone colors Green Olive 17-0535, Water Cress 17-0220 and Faded Rose 18-1629.

Stamen:
a. *Length*.—5.31 mm.
b. *Number per flower*.—12.
c. *Filament color*.—Pantone color Celery Green 13-0532.

Pistil:
a. *Length*.—7.06 mm.
b. *Ovary color* (*exterior*).—Pantone color Green Oasis 15-0538.
c. *Style length*.—8.51 mm.

Anther:
a. *Length*.—4.51 mm.
b. *Number*.—2 per stamen.
c. *Color*.—Pantone color Apricot Orange 17-1353.

Pollen:
a. *Abundance*.—Moderate.
b. *Color*.—Pantone colors Apricot Orange 17-1353.
c. *Self-fertility*.—Very good with approximately 87% self-pollinated flowers reaching maturity.

FRUIT

General:
a. *Time of fruit ripening*.—Mid season in Lowell, Oreg.
b. *Time of* 50% *maturity*.—Approximately early to mid-July in Lowell, Oreg.
c. *Fruit development period*.—67 days in Lowell, Oreg. in 2017.
d. *Mean harvest date*.—July 10.
e. *Mean date last pick*.—August 5.
f. *Cluster density*.—Moderate-high.
g. *Berries per cluster*.—8 berries per cluster.
h. *Unripe fruit color*.—Pantone colors Green Apple 15-0543, Mineral Red 17-1537, Baked Apple 18-1648.
i. *Ripe berry color*.—Pantone color Blue Ice 17-3922.
j. *Berry skin color after polishing*.—Pantone color Dark Navy 19-4013.
k. *Berry surface wax abundance*.—Heavy.
l. *Berry flesh color*.—Pantone colors Pale Star 12-0626 to Vanilla 12-0712.
m. *Berry weight*.—Average 1.80 g.
n. *Berry height from calyx to scar*.—12.73 mm.
o. *Berry diameter*.—18.20 mm.
p. *Calyx aperture*.—Average 6.04 mm.
q. *Calyx depth*.—Average 2.15 mm.
r. *Pedicel length*.—Average 10.90 mm.
s. *Pedicel surface texture*.—Smooth.
t. *Berry detachment force*.—Easy.
u. *Berry shape*.—Oblate.
v. *Fruit stem scar*.—Small, dry.
w. *Sweetness when ripe*.—Medium.
x. *Firmness when ripe*.—High.
y. *Acidity when ripe*.—Low.
z. *Storage quality*.—Very good.

SEED

General:
a. *Seed abundance in fruit*.—Moderate.
b. *Seed color*.—Pantone color Madder Brown 19-1331.
c. *Seed dry weight*.—0.40 mg. per seed.
d. *Seed length*.—Average 1.70 mm.

COMPARISON WITH PARENTAL AND COMMERCIAL CULTIVARS

TABLE 1

Comparison Table

| Denomination of similar variety | Characteristic for comparison | State of expression of similar variety | State of expression of candidate variety 'ZF08-029' |
|---|---|---|---|
| 'Draper' (U.S. Pat. No. PP15,103) | Fruit size | Large (18.6 mm/2.4 g) | Medium (17.4 mm/1.8 g) |
| 'Legacy' (not patented) | Firmness | Firm (248.78 g/mm) | Firm (248.88 g/mm) |

TABLE 1-continued

Comparison Table

| Denomination of similar variety | Characteristic for comparison | State of expression of similar variety | State of expression of candidate variety 'ZF08-029' |
|---|---|---|---|
| 'G-344' (not patented) | Vigor | Moderate | High |
| 'Draper' | Growth habit | Upright to Semi-sprawl | Round |

The invention claimed is:

1. A new and distinct variety of blueberry plant named 'ZF08-029', substantially as illustrated and described herein.

* * * * *